United States Patent [19]

Murata

[11] Patent Number: 5,210,189
[45] Date of Patent: May 11, 1993

[54] DNA SEQUENCE ENCODING GLYCEROL 3-PHOSPHATE ACYLTRANSFERASE

[76] Inventor: Norio Murata, 14-64, Fubuki-Cho, Okazaki-Shi, Aichi-Ken, Japan

[21] Appl. No.: 587,676

[22] Filed: Sep. 25, 1990

[30] Foreign Application Priority Data

Jan. 12, 1990 [JP] Japan ................................ 2-4782
Jul. 6, 1990 [JP] Japan ................................ 2-179088

[51] Int. Cl.$^5$ ............................................ C12N 15/29
[52] U.S. Cl. ................................ 536/23.2; 435/69.1; 435/252.3; 435/320.1
[58] Field of Search ............... 536/27; 435/172.3, 69.1, 435/252.3, 320.1

[56] References Cited

FOREIGN PATENT DOCUMENTS 1235594 3/1988 Japan .

OTHER PUBLICATIONS

Biochemistry, 18:5295–5299, 1979, Chirgwin et al Isolation of Biologically Active Ribonucleic Acid from Sources Enriched in Ribonuclease.
P.N.A.S. 84:6750–6754 Oct. 1987, LeGrand et al, Biological function of pathogenesis-related proteins: Four tobacco pathogenesis-related proteins are chitinases.
Plant Mol. Biol. 17:1067–1076, 1991, Weber et al. Purification and cDNA Sequencing of an Oleate-Selective Acyl-ACP:sn-glycerol-3-phosphate acyltransferase from pea . . . .
"Chilling Injury of Horticultural Crops", CRC Press, 1990, Wang ed. pp. 146–164.
Plant Physiol. 81:946–949, 1986, Kenrick et al The Fatty Acid Composition of Phosphatidylglycerol and Sulfoquinovosyldiacylglycerol of Higher Plants in Relation to Chilling Sensitivity.
Plant Physiol 68, 653–657, 1981 Betrams et al Positional Specificity and Fatty Acid Selectivity of Purified sn–Glycerol 3-Phosphate Acyltransferases from Chloroplasts.
A Simple and General Method for Transferring Genes into Plants Mar. 8, 1985, Science vol. 227 pp. 1229–1231.
Compositions and Positional Distributions of Fatty Acids in Phospholipids from Leaves of Chilling-Sensitive and Chilling-Resistant Plants, Plant & Cell Physiol. 23(6): 1071–1079 (1982).
David C. James and John T. Rossiter: Cytochrome P-450 In *Brassica Napus* Seedlings, Proceedings of the Third International Congress of Plant Molecular Biology.
J. P. Metraux et al.: Isolation of a complementary DNA encoding a chitinase with structural homology to a bifunctional lysozyme/chitinase, Proc. Natl. Acad. Sci. USA 86, 896–900, 1989.
Frentzen, M. et al, Eur. J. Biochem., 129: 629–636, "Specificities and Selectivities . . . ".
Vanden Broeck, G. et al., Nature 313:358–363 (1985) "Targeting of a foreign protein . . . ".
Okayama, H. et al, Mol. Cell. Biol., 2:161–170 (1982) "High-efficiency Cloning . . . ".
Ausubel, F. M. et al, "Current Protocols . . . "pp. 2 3.1–2.3.3. 4.31–434 1987.

(List continued on next page.)

Primary Examiner—Robert J. Hill, Jr.
Assistant Examiner—John D. Ulm
Attorney, Agent, or Firm—Ladas & Parry

[57] ABSTRACT

Disclosed is a DNA sequence which comprises a nucleotide sequence coding for a polypeptide having glycerol 3-phosphate acyltransferase activity and having the amino acid sequence corresponding substantially to the amino acid sequence from A to B represented in FIGS. 1(a) and (b). The DNA sequence has an ability to biotechnologically produce a glycerol 3-phosphate acyltransferase.

2 Claims, 16 Drawing Sheets

OTHER PUBLICATIONS

Tabor, S. et al, Proc. Natic. Acad. Sci. U.S.A. 84:4767–4771 (1987) "DNA Sequence . . . ".

Hanley, B. A. et al Nucleic Acids Research; 16:7159–7176 (1988) "Plant Intron sequences . . . ".

Wolf, S. F. et al, Nucleic Acids Res., 15:2911–1916 (1987) "Rapid hybridization Kinetics of DNA . . . ".

Maniatis, T. "Molecular Cloning" pp. 250–251 (1982).

Nishida, I. et al., Plant Cell Physiol., 28:1071–1079 (1987) "Purification of Isomeric . . . ".

Frentzen, M. et al., Plant Cell Physiol., 28:1195–1201 (1207) "Properties of the Plastidial . . . ".

Ishizaki, O. et al., 238, No. 2, 424–430 (1988) "Cloning and nucleotide . . . ".

Kranz et al. pp. 0.1–2.2 "Genetic resources . . . ". 0.1–2.2, Arabidopsis Info. Svc. (1987).

FEBS Lett. 238:424–430, Oct. 1988, Ishizaki et al. Cloning and nucleotide sequence of cDNA for the plastid glycerol-3-phosphate acyltransferase from squash.

R.N.A.S. 83:1408–1412, Mar. 1986, Chang et al, Molecular Cloning and DNA sequence of the *Arabidopsis thaliana* alcohol dehydrogenase gene.

```
         10        20        30        40        50
ATGACTCTCACGTTTTCCTCCTCCGCCGCAACCGTTGCCGTTGCTGCTGCA
MetThrLeuThrPheSerSerSerAlaAlaThrValAlaValAlaAlaAla
↑
C'

100       110       120       130       140
GCTTCGTCGACTCTTCGTGGATTAGTATCTTTCAGATTAACCGCGAAGAAG
AlaSerSerThrLeuArgGlyLeuValSerPheArgLeuThrAlaLysLys 190       200       210       220       230
GTGAGAGCCATGTCTGAGCTAGTTCAAGATAAAGAATCGTCCGTCGCGGCG
ValArgAlaMetSerGluLeuValGlnAspLysGluSerSerValAlaAla
         ↑
         C 280       290       300       310       320
GAGCTTAATCATTCCCGTACTTTCTTGGATGCGCGAAGTGAACAAGATCTT
GluLeuAsnHisSerArgThrPheLeuAspAlaArgSerGluGlnAspLeu
↑
A 370       380       390       400       410
CCAGCAAATGTTGCAGCAGGAATGGAAGAATTGTATTGGAACTACAAAAAT
ProAlaAsnValAlaAlaGlyMetGluGluLeuTyrTrpAsnTyrLysAsn 460       470       480       490       500
GTTGTATCAAACATGTCTGTTGCTTTTGATCGCATGCTTCTTGGTGTGGAG
ValValSerAsnMetSerValAlaPheAspArgMetLeuLeuGlyValGlu 550       560       570       580       590
GAACCATTTGACTACTACATGTTTGTCCATACATACATCCGTCCTCTTATT
GluProPheAspTyrTyrMetPheValHisThrTyrIleArgProLeuIle 640       650       660       670       680
TCTGAGCTGGAAGACAAGATTCGACAGGGACACAATATCGTGTTGATATCA
SerGluLeuGluAspLysIleArgGlnGlyHisAsnIleValLeuIleSer
```

FIG. 1A

```
                60            70            80            90
         ACCGTAACCTCCTCCGCTAGGGTTCCGGTTTATCCACTC
         ThrValThrSerSerAlaArgValProValTyrProLeu 150           160           170           180
         CTGTTTCTGCCGCCTCTTCGTTCTCGCGGCGGCGTTAGT
         LeuPheLeuProProLeuArgSerArgGlyGlyValSer 240           250           260           270
         AGCATTGCTTTCAATGAAGCCGCCGGTGAGACGCCGAGT
         SerIleAlaPheAsnGluAlaAlaGlyGluThrProSer 330           340           350           360
         TTATCTGGTATCAAGAAGGAAGCTGAAGCTGGAAGGTTG
         LeuSerGlyIleLysLysGluAlaGluAlaGlyArgLeu 420           430           440           450
         GCAGTTTTAAGTAGTGGAGCTTCCAGGGCAGATGAAACT
         AlaValLeuSerSerGlyAlaSerArgAlaAspGluThr 510           520           530           540
         GATCCTTATACTTTTAATCCATATCATAAAGCAGTCAGA
         AspProTyrThrPheAsnProTyrHisLysAlaValArg 600           610           620           630
         GATTTCAAAAATTCGTACGTTGGAAATGCTTCTATATTC
         AspPheLysAsnSerTyrValGlyAsnAlaSerIlePhe 690           700           710           720
         AACCATCAAAGTGAAGCTGATCCGGCTGTCATTTCTCTA
         AsnHisGlnSerGluAlaAspProAlaValIleSerLeu
                        FIG. IA CONT.
```

```
         730        740       750        760       770
TTGCTTGAAGCACAATCTCCTTTCATAGGAGAGAACATTAAATGTGTGGCT
 LeuLeuGluAlaGlnSerProPheIleGlyGluAsnIleLysCysValAla 820        830       840        850       860
AGTATGGAAGGAACCTCATATGTGTTTACTCGAAAAAGCACATGAATGTT
 SerMetGlyArgAsnLeuIleCysValTyrSerLysLysHisMetAsnVal 910        920       930        940       950
CGAAGCTTAAAGGAGATGGCTACAATGCTAAGGTCTGGCGGTCAACTTATA
 ArgSerLeuLysGluMetAlaThrMetLeuArgSerGlyGlyGlnLeuIle 1000       1010      1020       1030      1040
TCTACTGGGGAATGGTTTCCTGCACCCTTTGATGCTTCTTCGGTAGACAAC
 SerThrGlyGluTrpPheProAlaProPheAspAlaSerSerValAspAsn 1090       1100      1110       1120      1130
ATATATCCAATGTCTTTGCTTTGCTATGACATCATGCCCCCTCCACCCCAG
 IleTyrProMetSerLeuLeuCysTyrAspIleMetProProProProGln 1180       1190      1200       1210      1220
CACGGTACTGGACTATCAATTGCTCCTGAAATCAACTTCTCAGACGTCACA
 HisGlyThrGlyLeuSerIleAlaProGluIleAsnPheSerAspValThr 1270       1280      1290       1300      1310
AGCCAAGCTTTGTACAAGTCGGTGAATGAACAATACGAGATCTTAAACTCT
 SerGlnAlaLeuTyrLysSerValAsnGluGlnTyrGluIleLeuAsnSer 1360       1370      1380
AGGGTCTCTTTGTCACAACCTTGGAATTAG               FIG.IB
 ArgValSerLeuSerGlnProTrpAsn***
                            ↑
                            B
```

```
          780          790          800          810
GGTGATCGAGTCATCACTGATCCTCTTTGTAAGCCGTTC
GlyAspArgValIleThrAspProLeuCysLysProPhe 870          880          890          900
GATCCTGAGCTTGTTGACATGAAAAGAAAAGCAAACACA
AspProGluLeuValAspMetLysArgLysAlaAsnThr 960          970          980          990
TGGATTGCACCAAGCGGTGGAAGGGACCGCCCGAATCCT
TrpIleAlaProSerGlyGlyArgAspArgProAsnPro 1050         1060         1070         1080
ATGAGAAGACTGGTTGAACATTCTGGCGCTCCTGGACAT
MetArgArgLeuValGluHisSerGlyAlaProGlyHis 1140         1150         1160         1170
GTTGAGAAAGAAATCGGAGAGAAAGATTAGTTGGGTTT
ValGluLysGluIleGlyGluLysArgLeuValGlyPhe 1230         1240         1250         1260
GCAGACTGCGAGAGCCCTAATGAGGCGAAAGAAGCATAC
AlaAspCysGluSerProAsnGluAlaLysGluAlaTyr 1320         1330         1340         1350
GCGATTAAACACAGAAGAGGAGTAGAAGCATCAACTTCA
AlaIleLysHisArgArgGlyValGluAlaSerThrSer
```

*FIG. IB CONT.*

```
           10         20         30         40         50
       TATTCATTATGTGTACACACAAACATGACTACTTCAAACAAACACAAAGG 100        110        120        130        140
       AAAGATGTGAGGTTATAATTTGGTCTTGAGTCTTCTTTACTCACAAAGTC 190        200        210        220        230
       TATCATTATAATTATGAGTTCTTCAATGAAATAAGTTTACTAAGGGGAAA 280        290        300        310        320
       AAAAATAAAAAAGAAAAACGTGAAAAAGAGGGACTCATGGGATAAATAAA 370        380        390        400        410
       CACACGCTCTGCTTCGACCAATCACCAAACACGCTTTAATGACTCTCACG
                                           ↑MetThrLeuThr
                                           F'

460        470        480        490        500
       CCGTAACCTCCTCCGCTAGGGTTCCGGTTTATCCACTCGCTTCGTCGACT
       hrValThrSerSerAlaArgValProValTyrProLeuAlaSerSerThr 550        560        570        580        590
       TGTTTCTGCCGCCTCTTCGTTCTCGCGGCGGCGTTAGTGTGAGAGCCATG
       euPheLeuProProLeuArgSerArgGlyGlyValSerValArgAlaMet
                                                        ↑
                                                        F 640        650        660        670        680
       GCATTGCTTTCAATGAAGCCGCCGGTGAGACGCCGAGTGAGCTTAATCAT
       erIleAlaPheAsnGluAlaAlaGlyGluThrProSerGluLeuAsnHis
                                                ↑
                                                D 730        740        750        760        770
       TACTCTTCTTCGTCTTCTTTCCTGAGGAATTTGAATTGACTTGTGGTAGC 820        830        840        850        860
       TCCTTTGTGTTCATAATCTTATCGCGAAATCGATATTTGAGTTTGTTTCT 910        920        930        940        950
       TTTGCTTCTGATCTTGCTCCATTCTTGTTAAATGGATAAGAACGTCTTTG
                          FIG.2A
```

```
           60         70         80         90
     CAAATACAATGTACGGACGCAACTAACAAAAAATAAAAAT 150        160        170        180
     ACAATATCTAAATTTTATTAAATTTAAAATTAATACATAG 240        250        260        270
     TTAAATTAAATTATTAAAAAAAGAGTATTTAATTTGGTG 330        340        350        360
     AAGGAAGGAAGAGATCTCCGTCACACACACATAAACACTC 420        430        440        450
     TTTTCCTCCTCCGCCGCAACCGTTGCCGTTGCTGCTGCAA
     PheSerSerSerAlaAlaThrValAlaValAlaAlaAlaT 510        520        530        540
     CTTCGTGGATTAGTATCTTTCAGATTAACCGCGAAGAAGC
     LeuArgGlyLeuValSerPheArgLeuThrAlaLysLysL 600        610        620        630
     TCTGAGCTAGTTCAAGATAAAGAATCGTCCGTCGCGGCGA
     SerGluLeuValGlnAspLysGluSerSerValAlaAlaS 690        700        710        720
     TCCCGTACTTTCTTGGATGCGCGAAGTGAACAAGGTTAGT
     SerArgThrPheLeuAspAlaArgSerGluGlnA 780        790        800        810
     AATTCGGAAATGGAATTTAGAGTTGTGGAGATTGTTCGAT 870        880        890        900
     TGTTTGACTGGATAAGGTTCATTGAATTGACTTCTTGCCT 960        970        980        990
     GAATTCTTAGGTTGTGTTGCTCTTGATATGCTTTCGCTTT
```

*FIG. 2A CONT.*

```
          1000        1010        1020        1030         1040
   CTTTAAGAAAGATCAGTTCATAAGGATGCAATCAGATAATTTCCTTTTTC 1090        1100        1110        1120         1130
   TGCTTGTATTAACATTGTGTTTATCTTCATTTCCATCGTCAGATCTTTTA
                                                    spLeuLeu 1180        1190        1200        1210         1220
   CAAATGTTGCAGCAGGAATGGAAGAATTGTATTGGAACTACAAAAATGCA
   laAsnValAlaAlaGlyMetGluGluLeuTyrTrpAsnTyrLysAsnAla 1270        1280        1290        1300         1310
   AGTGCTATGCTTTGGAATTAATTAGATTAAAGAACATCAGTCCACTGAAC 1360        1370        1380        1390         1400
   TAGTGGAGCTTCCAGGGCAGATGAAACTGTTGTATCAAACATGTCTGTTG
   rSerGlyAlaSerArgAlaAspGluThrValValSerAsnMetSerValA 1450        1460        1470        1480         1490
   GTCAATCTCTTGGAATGATTTTTCTACTAGGAGATGTCATCTAAAAATTC 1540        1550        1560        1570         1580
   CTTATACTTTTAATCCATATCATAAAGCAGTCAGAGAACCATTTGACTAC
   roTyrThrPheAsnProTyrHisLysAlaValArgGluProPheAspTyr 1630        1640        1650        1660         1670
   TCAAGTAAGCTGGAATATGCACTCATAGTTATCAGATTTTATTCATAACT
   heLy 1720        1730        1740        1750         1760
   GATCTTCCAGTTTTCTTCTTGCCATCAAGTGTTCATCTACTAACAACCCT
```

*FIG. 2B*

```
          1050        1060        1070        1080
    AAAAAGTGCAAGTAGGAGTTTCTGGATGGATGTGTAACAA 1140        1150        1160        1170
    TCTGGTATCAAGAAGGAAGCTGAAGCTGGAAGGTTGCCAG
    SerGlyIleLysLysGluAlaGluAlaGlyArgLeuProA 1230        1240        1250        1260
    GTAAATGAATCCTTTTATCACTCACTAGTTTGTACGATTT 1320        1330        1340        1350
    TTTGGCATTGTTGTCTTACTGATGGTTTTTAGGTTTTAAG
                                      ValLeuSe 1410        1420        1430        1440
    CTTTTGATCGCATGCTTCTTGGTGTGGAGGTACTTCTTCT
    laPheAspArgMetLeuLeuGlyValGlu 1500        1510        1520        1530
    TTTTACTTGAGCTTCCTTGCGCTGTGAATATTTCAGGATC
                                          AspP 1590        1600        1610        1620
    TACATGTTTGTCCATACATACATCCGTCCTCTTATTGATT
    TyrMetPheValHisThrTyrIleArgProLeuIleAspP 1680        1690        1700        1710
    GAATGTAATTAGAAAGCAATATCGTTTGGTTAGTATCATG 1770        1780        1790        1800
    TGAATATGTTATGCAGAAATTCGTACGTTGGAAATGCTTC
                    sAsnSerTyrValGlyAsnAlaSe
```

FIG 2B CONT.

```
        1810       1820       1830       1840       1850
TATATTCTCTGAGCTGGAAGACAAGATTCGACAGGTCATCTTCCCTCTTT
rIlePheSerGluLeuGluAspLysIleArgGln 1900       1910       1920       1930       1940
AAAGTTCTTTCCATTCAGGATTTTAATACTCAACTGTTTAATTACAGGGA
                                                Gly 1990       2000       2010       2020       2030
ATCCGGCTGTCATTTCTCTATTGCTTGAAGCACAATCTCCTTTCATAGGA
spProAlaValIleSerLeuLeuGluAlaGlnSerProPheIleGly 2080       2090       2100       2110       2120
TACGCTATTGTCTCTGTTCTTATTTGTTTCTTTGGTTGCAGAAATGTGTG
                                           LysCysVal 2170       2180       2190       2200       2210
TCAGTATGGGAAGGTATCACGAGCTTTCATTTGCAATGGTATGCTACCTG
heSerMetGlyAr 2260       2270       2280       2290       2300
GGATTTCTACTGCTTTCAGGAACCTCATATGTGTTTACTCGAAAAAGCAC
       gAsnLeuIleCysValTyrSerLysLysHis 2350       2360       2370       2380       2390
CAAACACACGAAGCTTAAAGGAGATGGCTACAATGCTAAGGTTAATGGAA
laAsnThrArgSerLeuLysGluMetAlaThrMetLeuAr 2440       2450       2460       2470       2480
AATTAAAGGAAAACATTGATGTTTAGTCTGCTAATGTTGATGAACCCTGT 2530       2540       2550       2560       2570
GAAGGGACCGCCCGAATCCTTCTACTGGGGAATGGTTTCCTGTAAGTTAT
lyArgAspArgProAsnProSerThrGlyGluTrpPhePro
```

FIG. 2C

```
              1860        1870        1880       1890
        CTTGTGCTCTAGTTAATGCTGTTTGCTTTCATCAACAGTT 1950        1960        1970       1980
        CACAATATCGTGTTGATATCAAACCATCAAAGTGAAGCTG
        HisAsnIleValLeuIleSerAsnHisGlnSerGluAlaA 2040        2050        2060       2070
        GAGAACATTGTGAGCCTTCGAGCCTTGTTCTGAGCTATTA
        GluAsnIle 2130        2140        2150       2160
        GCTGGTGATCGAGTCATCACTGATCCTCTTTGTAAGCCGT
        AlaGlyAspArgValIleThrAspProLeuCysLysProP 2220        2230        2240       2250
        ATGGGCTGAAGTGTAATCTTAGCACCTTGTATGACTTCCG 2310        2320        2330       2340
        ATGAATGTTGATCCTGAGCTTGTTGACATGAAAAGAAAAG
        MetAsnValAspProGluLeuValAspMetLysArgLysA 2400        2410        2420       2430
        CTAAATAGCGAGTGTTCTTATTTGATCTCATAGGAACAGA 2490        2500        2510       2520
        AGGTCTGGCGGTCAACTTATATGGATTGCACCAAGCGGTG
         gSerGlyGlyGlnLeuIleTrpIleAlaProSerGlyG 2580        2590        2600       2610
        TTGATGGAATACAGAGATCTTATCTGAGTCTGGTAGATAT
```

*FIG. 2C CONT.*

```
          2620        2630        2640        2650        2660
GCAAGTACTAATCTAGTAATGTTCAGGCACCCTTTGATGCTTCTTCGGTA
AlaProPheAspAlaSerSerVal 2710        2720        2730        2740        2750
GACATATATATCCAATGTCTTTGCTTTGCTATGACATCATGCCCCCTCCA
lyHisIleTyrProMetSerLeuLeuCysTyrAspIleMetProProPro 2800        2810        2820        2830        2840
CCGTTTTGGGCTAACTCTGGTTGACTTTCCTCTCATCATCACTTCATTGT 2890        2900        2910        2920        2930
AGTTGGGTTTCACGGTACTGGACTATCAATTGCTCCTGAAATCAACTTCT
uValGlyPheHisGlyThrGlyLeuSerIleAlaProGluIleAsnPheS 2980        2990        3000        3010        3020
TCTGTAACACTCAGCACACCAATGACTTTAGTTTCAAGATCGAGTAATTC 3070        3080        3090        3100        3110
AGAAGCATACAGCCAAGCTTTGTACAAGTCGGTGAATGAACAATACGAGA
sGluAlaTyrSerGlnAlaLeuTyrLysSerValAsnGluGlnTyrGluI 3160        3170        3180        3190        3200
ATCAACTTCAAGGGTCTCTTTGTCACAACCTTGGAATTAGTCTCTCGTTT
aSerThrSerArgValSerLeuSerGlnProTrpAsn***
                                       ↑
                                       E 3250        3260        3270        3280        3290
AAGTTTTGTTGCAACTGTATATATATTGAGAGAGAGCATTGTTCTTTC 3340        3350        3360        3370        3380
AAAAAAAAAAATGGAGATATTATTCACACGTTGTCCTAGGGAGTTTTTTTT
```

FIG. 2D

```
           2670        2680        2690        2700
GACAACATGAGAAGACTGGTTGAACATTCTGGCGCTCCTG
AspAsnMetArgArgLeuValGluHisSerGlyAlaProG 2760        2770        2780        2790
CCCCAGGTATTGATTGTTTTCTTCTCTCTGTCTCTCTTCT
ProGln 2850        2860        2870        2880
GCATCTGCCAGGTTGAGAAAGAAATCGGAGAGAAAAGATT
           ValGluLysGluIleGlyGluLysArgLe 2940        2950        2960        2970
CAGACGTCACAGCAGACTGCGAGAGCCCTAATGAGGTCTG
erAspValThrAlaAspCysGluSerProAsnGlu 3030        3040        3050        3060
ATCATGCATATAAATACATTCTTGTGGTATGGCAGGCGAA
                                     AlaLy 3120        3130        3140        3150
TCTTAAACTCTGCGATTAAACACAGAAGAGGAGTAGAAGC
leLeuAsnSerAlaIleLysHisArgArgGlyValGluAl 3210        3220        3230        3240
TAGGGTAACACTTTCAAAACTCATAAATCTTCTGTCTCAG 3300        3310        3320        3330
ATTTGCAGGATACACAAACACAATCAATGGAAAATACTCA

3390
TTTTTTCAACGAGTTCC
```

*FIG 2D CONT.*

```
  1 ACCAAACACGCTTTAATGACTCTCACGTTTCCTCCTCCGCCCGCAACCGTTGCCGTTGCT   60
                MetThrLeuThrPheSerSerAlaAlaThrValAlaValAla

61 GCTGCAACCGTAACCTCCTCCGCTAGGGTTCCGGTTTATCCACTCGTCGTCGACTCTT   120
    AlaAlaThrValThrSerSerAlaArgValProValTyrProLeuAlaSerSerThrThrLeu

121 CGTGGATTAGTATCTTTCAGATTAACCGCGAAGAAGCTGTTTCTGCGCCTCTTCGTTCT   180
    ArgGlyLeuValSerPheArgLeuThrAlaLysLysLeuPheLeuProProLeuArgSer

181 CGCGGGCGGCGTTAGTGTGAGAGCCATGTCTGAGCTAGTTCAAGATAAAGAATCGTCCGTC   240
    ArgGlyGlyValSerValArgAlaMetSerGluLeuValGlnAspLysGluSerSerVal

241 GCGGCGAGCATTGCTTTCAATGAAGACCCGGTGAGAGCCGAGTTAATCATTCC   300
    AlaAlaSerIleAlaPheAsnGluAlaAlaGlyGluThrProSerGluLeuAsnHisSer

301 CGTACTTTCTTGGATGCGCGAAGTGAACAAGATCTTTATCTGGTATCAAGAAGGAAGCT   360
    ArgThrPheLeuAspAlaArgSerGluGlnAspLeuLeuSerGlyIleLysLysGluAla
```

*FIG. 3A*

361 GAAGCTGGAAGGTTGCCAGCAAATGTTGCAGCAGGAATGGAAGAATTGTATTGGAACTAC     420
    GluAlaGlyArgLeuProAlaAsnValAlaAlaGlyMetGluGluLeuTyrTrpAsnTyr

421 AAAAATGCAGTTTTAAGTAGTGGAGCTTCCAGGGCAGATGAAACTGTTATCAAACATG      480
    LysAsnAlaValLeuSerSerGlyAlaSerArgAlaAspGluThrValValSerAsnMet

481 TCTGTTGCTTTTGATCGCATGCTTCTTGGTGTGGAGGATCCTTATACTTTTAATCCATAT    540
    SerValAlaPheAspArgMetLeuLeuGlyValGluAspProTyrThrPheAsnProTyr

541 CATAAAGCAGTCAGAGAACCATTTGACTACTACATGTTTGTCCATACATACATCCGTCCT    600
    HisLysAlaValArgGluProPheAspTyrTyrMetPheValHisThrTyrIleArgPro

601 CTTATTGATTTCAAAAATTCGTACGTTGGAAATGCTTCTATATTCTCTGAGCTGGAAGAC    660
    LeuIleAspPheLysAsnSerTyrValGlyAsnAlaSerIlePheSerGluLeuGluAsp

661 AAGATTCGACAGGGACACAATATCGTGTTGATATCAAACCATCAAAGTGAAGCTGATCCG    720
    LysIleArgGlnGlyHisAsnIleValLeuIleSerAsnHisGlnSerGluAlaAspPro

FIG. 3A CONT.

```
721  GCTGTCATTTCTCTATTGCTTGAAGCACAATCTCCTTCATAGGAGAGAACATTAAATGT  780
     AlaValIleSerLeuLeuLeuGluAlaGlnSerProPheIleGlyGluAsnIleLysCys

781  GTGGCTGGTGATCGAGTCATCACTGATCCTCTTTGTAAGCCGTTCAGTATGGGAAGGAAC  840
     ValAlaGlyAspArgValIleThrAspProLeuCysLysProPheSerMetGlyArgAsn

841  CTCATATGTGTTTACTCGAAAAAGCACATGAATGTTGATCCTGAGCTTGTTGACATGAAA  900
     LeuIleCysValTyrSerLysLysHisMetAsnValAspProGluLeuValAspMetLys

901  AGAAAAGCAAACACACGAAGCTTAAAGGAGATGGCTACAATGCTAAGGTCTCGGCGGTCAA  960
     ArgLysAlaAsnThrArgSerLeuLysGluMetAlaThrMetLeuArgSerGlyGlyGln

961  CTTATATGGATTGCACCAAGCGGTGGAAGGGACCGCCCGAATCCTTCTACTGGGAATGG  1020
     LeuIleTrpIleAlaProSerGlyArgAspArgProAsnProSerThrGlyGluTrp

1021 TTTCCTGCACCCTTTGATGCTTCTTCGGTAGACAACATGAGAAGACTGGTTGAACATTCT  1080
     PheProAlaProPheAspAlaSerSerValAspAsnMetArgArgLeuValGluHisSer
```

FIG 3B

1081 GGCGCTCCTGGACATATATATCCAATGTCTTTGCTATGACATCATGCCCCCTCCA 1140
     GlyAlaProGlyHisIleTyrProMetSerLeuLeuCysTyrAspIleMetProProPro

1141 CCCCAGGTTGAGAAAGAAATCGGAGAGAAAAGATTAGTTGGGTTTCACGGTACTGGACTA 1200
     ProGlnValGluGluLysGluIleGlyGluLysArgLeuValGlyPheHisGlyThrGlyLeu

1201 TCAATTGCTCCTGAAATCAACTTCTCAGACGTCACAGCAGACTGCGAGAGCCCTAATGAG 1260
     SerIleAlaProGluIleAsnPheSerAspValThrAlaAspCysGluSerProAsnGlu

1261 GCGAAAGAAGCATACAGCCAAGCTTTGTACAAGTCGGTGAATGAACAATACGAGATCTTA 1320
     AlaLysGluAlaTyrSerGlnAlaLeuTyrLysSerValAsnGluGlnTyrGluIleLeu

1321 AACTCTGCGATTAAACACAGAAGAGGAGTAGAAGCATCAACTTCAAGGGTCTCTTTGTCA 1380
     AsnSerAlaIleLysHisArgArgGlyValGluAlaSerThrSerArgValSerLeuSer

1381 CAACCTTGGAATTAGTCTCTCGTTTTAGGGATACACAAACACAATCAATGGAAAATACTC 1440
     GlnProTrpAsn***

1441 AAAAA 1445

FIG. 3B CONT.

DNA SEQUENCE ENCODING GLYCEROL 3-PHOSPHATE ACYLTRANSFERASE

BACKGROUND OF THE INVENTION

1. Field of the Art

The present invention relates to an isolated DNA sequence coding for a polypeptide which has enzymatic activity of glycerol 3-phosphate acyltransferase (referred to hereinafter as ATase) as is produced by *Arabidopsis thaliana* Heynhold.

2. Related Art

Lipid components of the plant biomembranes change from a liquid-crystalline phase to a gel phase when the environmental temperature decreases, which is accompanied by changes in the properties of these biomembranes. It is presumed that the biomembranes cannot fulfill its intact functions in the gel phase as they lose the selective permeability, which results in disfunctions of cells. Among the lipids, phosphatidylglycerol (referred to hereinafter as PG) changes from the liquid-crystalline phase to the gel phase at a high temperature and thus tends to gelate at a high temperature. Therefore, the temperature sensitivity of biomembranes greatly varies with the properties of PG. In this connection, the tendency of gelation of PG molecules depends on the composition of fatty acids that constitutes the PG. The transfer of an acyl-group to glycerol 3-phosphate (referred to hereinafter as G-3-P) is carried out by the ATase. That is, the transfer reaction of an acyl-group from an acyl-carrier protein (referred to hereinafter as ACP) to G-3-P is catalyzed by the ATase.

In plants, fatty acids are synthesized only in chloroplasts. Acyl-ACPs, the substrates of the ATase, are mainly palmitoyl-ACP (referred to hereinafter as 16:0-ACP) and oleoyl-ACP (referred to hereinafter as 18:1-ACP). The selection between these two substrates by the ATase depends on a property of the ATase itself, that is, substrate selectivity. The substrate selectivity of the ATase has been investigated for a variety of plants. For example, the ATase from chilling-resistant plants, spinach and pea, has a high substrate selectivity to the 18:1-ACP [Eur. J. Biochem., 129 (1983), 629–636], and the PG of these plants remains in liquid-crystalline phase even at a relatively low temperature. On the other hand, since the ATase from chilling-sensitive plants does not distinguish 18:1-ACP from 16:0-ACP and transfers both fatty acids in an almost equal proportion, the PG of squash gelates at a relatively high temperature (details will be described later).

Among the ATases of plants, that of squash, a chilling-sensitive plant, is the only one for which the complete amino acid sequence has been elucidated. The sequence has been applied for a patent as "a DNA sequence coding for glycerol 3-phosphate acyltransphe-rase" by the present inventor (Japanese Patent Laid-Open Publication No. 235594/1989). The complete amino acid sequence of an ATase from chilling-resistant plants is elucidated for the first time by the present invention in which the sequence is derived from the enzyme of *Arabidopsis thaliana* Heynhold. While the amino acid sequence of the ATase of *Arabidopsis thaliana* Heynhold is as a whole similar to that of squash, it has regions which are greatly different from that of squash. The difference in the substrate selectivity of the ATases is probably accounted for by this difference in the amino acid sequences.

It is indicated that a "transit peptide" is present at the N-terminal domain of proteins which are synthesized in cytoplasm and transferred to chloroplasts. It has been demonstrated that such a transit peptide is necessary for their transfer [Nature, 313 (1985), 358–363].

DISCLOSURE OF THE INVENTION

Outline of the Invention

The present invention provides an isolated DNA sequence coding for a polypeptide which has an enzymatic activity of those ATases that are useful for improving the properties of a membrane lipid, PG, in chloroplasts.

That is, the DNA sequence according to the present invention is characterized by that it includes a nucleotide sequence coding for a polypeptide which has a glycerol 3-phosphate acyltransferase activity and whose amino acid sequence corresponds substantially to the amino acid sequence from A to B shown in FIGS. 1(a) and (b).

Effect

The polypeptide or protein obtained by the expression of the DNA sequence according to the present invention has a glycerol 3-phosphate acyltransferase activity and exhibits a high substrate selectivity to 18:1-ACP (see Experimental Example 3 below).

Therefore, it is postulated that by the introduction and expression of the DNA sequence according to the present invention into a chilling-sensitive plant (containing a relatively large portion of saturated molecular species of PG), it will be possible to increase the content of unsaturated molecular species of the PG, that is, to make the content close to that in the fatty acid composition of chilling resistant plants. Techniques for introducing and expressing a DNA sequence in plants are general techniques which have already been practiced for many kinds of plants such as tobacco, petunia, potato and the like.

Further, it is postulated that the use of the DNA sequence obtained in the present invention as a probe facilitates to clone genes encoding the enzymes from chilling-resistant plants, which have a similar substrate selectivity, by the methods which are usually used in the field of genetic engineering.

BRIEF DESCRIPTION OF THE DRAWINGS

FIGS. 1(a)–(b) show an example of the amino acid sequence of a peptide containing as a portion the ATase which is an object of the present invention, and the nucleotide sequence coding for this amino acid sequence;

FIGS. 2(a)–(d) show the nucleotide sequence of genomic DNA containing the ATase gene of *Arabidopsis thaliana* Heynhold and obtained in Experimental Example 1 of the present invention, along with the amino acids encoded by the exon regions; and FIGS. 3(a)–(b) show the nucleotide sequence of cDNA containing the ATase gene of *Arabidopsis thaliana* Heynhold as a portion and obtained in Experimental Example 2 of the present invention, along with the amino acid sequence encoded.

DETAILED DESCRIPTION OF THE INVENTION

The ATase gene

Definition

The DNA sequence having an ability to biotechnologically produce the ATase according to the present invention, that is the ATase gene, codes for a polypeptide which has an ATase activity and whose amino acid sequence corresponds substantially to the amino acid sequence from A to B shown in FIGS. 1(a)–(b). The term "DNA sequence" herein means a polydeoxyribonucleotide chain having a certain length In the present invention, the "DNA sequence" is specified by the amino acid sequence of the polypeptide encoded by the DNA sequence, said amino acid sequence including modified sequences which will be described hereinafter. Since the polypeptide has a definite length, the "DNA sequence", which includes degenerated isomers which will be described hereinafter, has a definite length The DNA sequence of the present invention contains the gene encoding the ATase and is useful for the biotechnological production of this polypeptide. However, the biotechnological production of this polypeptide cannot be conducted only by the DNA sequence having a definite length defined by the length of the ATase; the presence of DNA sequences with an appropriate length are necessary at the 5'-upstream and 3'-downstream. The biotechnological production of the polypeptide is also possible when the DNA sequence encoding this polypeptide comprises the coding region in exons which are interrupted by several introns, and it is reported that the introns sometimes increase the level of gene expression (The abstracts of the 12th Annual Meeting of Molecular Biological Society, Japan, p. 240, 3J-23, 1989). As described above, a transit peptide of required at the N-terminus of the mature ATase for its transfer from cytoplasm to chloroplasts. Therefore, if the ATase synthesized in cytoplasm is required to be transferred to chloroplasts, the gene encoding the ATase needs to have a DNA sequence coding for a transmit peptide of the 5'-upstream.

Accordingly, the term "DNA sequence" in the present invention includes, in addition to the DNA sequence having a specific length [defined by the length of A to B of the corresponding polypeptide shown in FIGS. 1(a) and (b)], linear or circular DNA strand containing this DNA sequence of the specific length.

Typical existing forms of the DNA sequence according to the present invention are the DNA sequence inserted in plasmid or phase DNAs and the DNA sequence inserted in either plasmid, phage or genomic DNAs carried by either microorganisms (particularly bacteria), phage particles or plants. The bacteria herein include *Escherichia coli* and *Agrobacterium tumefaciens.*

A preferred existing form of the DNA sequence according to the present invention is the DNA sequence inserted into a plant genome, where it is aligned with other DNA sequences as follows in order to stably express the ATase: (in this order) a promoter, a DNA sequence of a regulatory region for translation, a DNA sequence coding for a transit peptide to chloroplasts, the DNA sequence according to the present invention, a DNA sequence coding for a termination codon, a DNA sequence coding for a poly(A)addition signal and a terminator. As the promoter, the DNA sequence of a regulatory region for translation, the DNA sequence coding for a termination codon, the DNA sequence coding for a poly(A)addition signal and the terminator, an appropriate combination of those which are well-known in the field can be used. The DNA sequence coding for a transit peptide to chloroplasts may be that of the ATase gene obtained in the present invention [nucleotide number 190-270 or 1-270 in FIG. 1(a)], or a well-known sequence such as that of the genes for the small subunits of ribulose-1,5-bisphosphate carboxylase/oxygenase of spinach.

Polypeptide encoded by the gene

As described above, the DNA sequence according to the present invention is specified by the polypeptide encoded. The polypeptide has an ATase activity, and its amino acid sequence corresponds substantially to the amino acid sequence from A to B shown in FIGS. 1(a) and (b). It is needless to say that FIG. 1(b) represents the continuation of FIG. 1(a). The phraseology "the amino acid sequence corresponds substantially to the amino acid sequence from A to B shown in FIGS. 1(a) and (b)" herein means that the polypeptide may have deletions, substitutions, additions or the like in some of the amino acids as far as the polypeptide possesses the ATase activity.

The part from C to A (or from C' to A) of the amino acid sequence represented in FIGS. 1(a) and (b) appears to be at least a part of the transit peptide by comparison with the ATase of squash. This part shall also include a variety of modifications of the amino acid sequence as described above.

The typical polypeptide having an ATase activity in the present invention corresponds to the amino acid sequence from A to B (or C to B, or C' to B) in FIGS. 1(a) and (b) and consists of 369 (or 396 or 459) amino acids, and such an amino acid sequence has not hitherto been reported.

The ATase as the object of the present invention is the enzyme specified as EC 2. 3. 1.15.

The Nucleotide sequence

The DNA sequence coding for the ATase includes the one which has the nucleotide sequence represented by A to B (or C to B, or C' to B) in FIG. 1 or degenerate isomers thereof as well as the ones which have the nucleotide sequence corresponding to the variations of the amino acid sequence of the ATase as described above or degenerate isomers thereof. The term "degenerate isomer" herein means a DNA sequence which is different from others only in the degenerate codons and codes for the same polypeptide. For instance, a DNA sequence having the nucleotide sequence from A to B (from C to B, or from C' to B) shown in FIG. 1 but a codon substitution of, for example, an AAC (corresponding to Asn) with an AAT, which is in the degenerate relationship with AAC, shall be referred to as a degenerate isomer in the present invention.

A preferred embodiment of the DNA sequence according to the present invention has at least one termination codon such as TAG next to the 3'-terminus. The 5'-upstream and/or 3'-downstream of the DNA sequence of the present invention may also be followed by DNA sequences (sequence) of a certain length as an untranslated regions (region).

Another preferred embodiment is a DNA sequence which includes the nucleotide sequence from A to B (or C to B, or C' to B) shown in FIG. 1 as the coding region in exons interrupted with one or more introns. This preferred embodiment is illustrated by D to E (or F to E, or F' to E) in FIG. 2. As the introns, well-known introns can be used appropriately in addition to those illustrated in FIG. 2 (see the abstract of the 12th Annual Meeting of Molecular Biological Society (described above), Japan).

The nucleotide sequence shown in FIGS. 2(a)-(d) was determined by the dideoxy termination method from the genomic DNA encoding the ATase obtained from the leaves and stems of seedlings of *Arabidopsis thaliana* Heynhold.

The nucleotide sequence shown in FIGS. 3(a)-(b) was determined by the dideoxy termination method from the cDNA coding for the ATase of *Arabidopsis thaliana* Heynhold.

Acquirement of the DNA sequence

One of the methods for acquiring a DNA sequence described above encoding the amino acid sequence of the ATase comprises the chemical synthesis of at least a part of the DNA sequence.

If one considers that the ATase has at least 369 amino acid residues, it is more preferable than the chemical synthesis to acquire the DNA sequence by genetic engineering processes. These processes comprise first constructing a cDNA library from mRNAs derived from the leaves and/or stems of *Arabidopsis thaliana* Heynhold by methods usually used in the field of genetic engineering such as the OKAYAMA-BERG method [Mol. Cell Biol., 2 (1982), 161–170] and then isolating the DNA sequence by widely used screening methods such as immunological screening and nucleic acid hybridization using appropriate probes.

In this connection, the present inventor had isolated the cDNA for the ATase derived from *Cucurbita moschata* Duch (see Japanese Patent Laid-Open Publication No. 235594/1989). The inventor then constructed a genomic DNA library derived from leaves and stems of *Arabidopsis thaliana* Heynhold seedlings using a λ phage vector which is usually used in the field of genetic engineering. By screening the library by the plaque hybridization method using the cDNA for the squash ATase labeled with a 32P radio isotope as a probe, the inventor obtained a genomic DNA sequence containing the DNA sequence of the present invention (see Experimental Example 1 below for details). Further, as an alternative to this, the present inventor obtained a cDNA clone containing the DNA sequence of the present invention from a cDNA library of *Arabidopsis thaliana* Heynhold using this genomic DNA as a probe (see Experimental Example 2 below for details).

*Arabidopsis thaliana* Heynhold, the source of the DNA sequence of the present invention, is a plant which grows naturally in Japan and is described in "MAKINO SHINSHOKUBUTSU ZUKAN", (Hokuryu-kan, 1982, p. 218). Its seeds are available from Arabidopsis Information Service (Prof. Dr. A. R. Kranz, Botanisches Institut, J. W. Goethe Universitaet, Siesmayerstr., 70, Postfach 111 932, D-6000 Frankfurt am Main 11, Federal Republic of Germany).

EXPERIMENTAL EXAMPLES

Experimental Example 1

Isolation of the ATase gene from a genomic DNA library of *Arabidopsis thaliana* Heynhold (1) Construction of a genomic DNA library (i) Preparation of genomic DNA Genomic DNA was obtained from about 10 g of leaves and stems of *Arabidopsis thaliana* Heynhold (Lansberg strain) as described in Current Protocols in Molecular Biology, Vol. 1, pp. 2,3,1–2,3,3 (Edited by F. M. Ausbel, R. Bront, R. E. Kingston, D. D. Moore, J. G. Seidman, J. A. Smith and K. Struhl, John Wiley and Sons, 1987).

(ii) Construction of genomic DNA library

The genomic DNA was partially digested with a restriction enzyme Sau3AI, inserted into the BamHI site of a lambda phage vector λDASH (Stratagene) and packaged in vitro using an in vitro packaging kit (GIGAPACK GOLD; Stratagene) to give a genomic DNA library in λ phage.

(2) Isolation of the ATase gene (i) Screening of clones retaining the ATase gene

*Escherichia coli* strain P2392 (Stratagene) was infected with the phage library, and three plates (10 cm ×14 cm) with $6 \times 10^3$–$6 \times 10^4$ plaques each were screened. The phages were transferred to filters, which were incubated at 68° C. for 2 hours in a hybridization solution containing 5 ×Denhart's solution (0.1% Ficoll, 0.1% polyvinylpyrrolidone, 0.1% bovine serum albumin), 6×SSC (900 mM NaCl, 90 mM trisodium citrate, pH 7.4), 10% dextran sulfate, 0.1% sodium dodecylsulfate and 100 μg/ml of salmon sperm DNA.

A cDNA fragment for the ATase of squash (*Cucurbita moschata* Duch) was obtained by excising, with a restriction enzyme EcoRI, from the recombinant plasmid pAT 03 carrying the cDNA for the squash ATase from *Escherichia coli* AT-03 [Deposit No.: FERM BP-3094 (Original Deposit No.: FERM P-9934); Deposit Date: Mar. 11, 1988; Indication for distinguishment: AT-03]. This cDNA fragment was subjected to nick translation (nick translation kit; Takara Shuzo) with $^{32}$P-dATP to give a probe with a specific activity of about $10^8$ dpm/μg.

The probe was added to the hybridization solution and the filters were further incubated in this solution at 50° C. for 12 hours. Then, the filters were washed at 40° C. with 2×SSC and 0.1% sodium dodecylsulfate solution and subjected to autoradiography to select phages which hybridized strongly to the probe.

The genomic DNA of *Arabidopsis thaliana* Heynhold was excised from the phage DNA with restriction enzymes BamHI and XbaI and subjected to 0.8% agarose gel electrophoresis to recover a 3.6 kbp DNA fragment (referred to hereinafter as BX3.6). This fragment strongly hybridized to the probe. It was subcloned to a plasmid vector pBLUESCRIPT (Stratagene) to give a plasmid pBX3.6. Similarly, a 2.6 kbp DNA fragment (referred to hereinafter as BB2.6) was excised from the phage DNA with a restriction enzyme BamHI and was subcloned to give a plasmid pBB2.6. The nucleotide sequences of the genomic DNA fragments of *Arabidopsis thaliana* Heynhold in pBX3.6 and pBB2.6 were analyzed by the dideoxy termination method (Proc. Natl.

Acad. Sci., USA, 84 (1987), 4767–4771). The DNA sequence with a total length of 3,397 bp which encompassed BX3.6 and BB2.6 contained several open reading frames (from F to E or from F' to E in FIG. 2) (in which the nucleotide Nos. 1–1526 and 1527–3397 are derived from BX3.6 and BB2.6, respectively). By the comparison of the nucleotide sequence of the open reading frames with that of the cDNA for the squash ATase, and by the search for the conserved exon-intron junction sequence [Nucl. Acids Res., 16 (1988), 7159–7176], a coding region consisting of 1,188 bp or 1,377 bp was found in exons. This is shown in FIG. 1. In consideration that this coding region in exons is highly homologous to the cDNA for the squash ATase in both the nucleotide and the amino acid sequences, it was deduced that the DNA sequence represented from C to B (or from C' to B) in FIG. 1 encodes the precursor of the ATase containing a transit peptide to chloroplasts, consisting of 396 (or 459) amino acids with a molecular mass of 43,955 (or 50,431). It was also found that DNA sequences consisting of 587 bp (or 398 bp) and 210 bp were present at the upstream (nucleotide Nos. 1–587 (or 1–398) in FIG. 2) and downstream (nucleotide Nos. 3188–3397 in FIG. 2) of the coding region, respectively. It is presumed that the upstream and/or downstream region contains at least a part of the regulatory regions for translation. In particular, a termination codon (which is the DNA strand of nucleotide Nos. 3188–3190 in FIG. 2) was present in the downstream region.

It is assumed that the amino acid sequences C - A (or C'- A) in FIG. 1(a) or F - D (or F'- D) in FIG. 2(a) is a transit peptide to chloroplasts by comparison with the squash ATase.

Experimental Example 2

Isolation of the ATase cDNA from a cDNA library of Arabidopsis thaliana Heynhold (1) Construction of a cDNA library (i) Preparation of RNA Total RNA was prepared from about 15 g of leaves and stems of Arabidopsis thaliana Heynhold (Lansberg strain) according to the method described in Current Protocols in Molecular Biology, Vol. 1, pp. 4.3.1–4.3.4 (Edited by F. M. Ausbel, R. Bront, R. E. Kingston, D. D. Moore, J. G. Seidman, J. A. Smith and K. Struhl, John Wiley and Sons, 1987). Poly(A)+RNA was prepared from the total RNA according to Wolf et al. (Nucl. Acids Res., 15 (1987), 2911–2926).

(ii) Construction of a cDNA library

DNA complementary to the above poly(A)+ RNA was synthesized according to the manual of the cDNA synthesis kit available from Pharmacia, using an oligo(dT) nucleotide as a primer. An EcoRI adapter containing a NotI recognition sequence (Pharmacia) was ligated at each terminus of the double strand cDNA thus synthesized, which was followed by ligation to the EcoRI site of a λ phage vector λZAPII (Stratagene). The phage DNA was packaged in vitro using an in vitro packaging kit (GIGAPACK II GOLD: Stratagene) to give a cDNA library in λZAPII.

(2) Isolation of the ATase cDNA (i) Screening of clones retaining the ATase cDNA Escherichia coli strain XL1-Blue (Stratagene) was infected by the λ phage library, and five plates (10 cm × 14 cm) with 2 × 10⁴ plaques each were screened. The phages were transferred to filters, which were incubated at 65° C. for 1 hour in a hybridization solution containing 6 × SSC (900 mM NaCl, 90 mM sodium citrate, pH 7.4), 0.05% skim milk and 0.02% sodium azide. A fragment of the genomic ATase gene of Arabidopsis thaliana Heynhold was obtained by excising, with a restriction enzyme BamHI, from the recombinant plasmid pBB2.6 carrying a fragment of the ATase gene of Arabidopsis thaliana Heynhold [Experimental Example 1(2)(i)]. This DNA fragment was subjected to nick translation (nick translation kit, Takara Shuzo) with $^{32}$P-dATP to give a probe with a specific activity of about $10^7$ dpm/μg.

The probe was added to the hybridization solution and the filters were further incubated in this solution at 65° C. for 16 hours. Then, the filters were washed at 65° C. with 1 × SSC and 0.1% sodium dodecylsulfate solution and subjected to autoradiography to select phages which hybridized strongly to the probe.

(ii) Structural analysis of the ATase cDNA

Inserts were excised from the phage DNAs with a restriction enzyme EcoRI and subjected to 1% agarose gel electrophoresis to determine the size of the fragments. It was found that one of the DNA fragments was about 1.4 kbp. This fragment was subcloned in a plasmid vector pBLUESCRIPT (Stratagene) to give a plasmid pARAT. The nucleotide sequence of the fragment was determined by the dideoxy termination method (Proc. Natl. Acad. Sci., USA, 84 (1987), 4767–4771) from pARAT.

As a result, it was found that the insert had a length of 1,445 bp which contains an open reading frame consisting of 1,188 bp or 1,377 bp, which is shown in FIG. 3. In consideration of a high homology of the open reading frame to the cDNA for the squash ATase in both the nucleotide and the amino acid sequences, it was deduced that the DNA sequence represented from I to H (or from I' to H) in FIGS. 3 (a)–(b) encodes the precursor of the ATase containing a transit peptide to chloroplasts, consisting of 396 (or 459) amino acids with a molecular mass of 43,955 (or 50,431). This sequence coincides completely with the coding region in exons deduced from the genomic DNA sequence represented by C to B (or C' to B) in FIGS. 1(a) and (b). It was also found that non-coding regions of 204 bp (or 15 bp) and 53 bp were present at the upstream (nucleotide Nos. 1–204 (or 1–15 in FIG. 3(a)) and downstream (nucleotide Nos. 1393–1445 in FIG. 3(b)) of the open reading frame, respectively. It is presumed that at least a part of the regulatory regions for translation is present in these upstream and/or downstream region. The open reading frame had a termination codon (which corresponds to the DNA sequence of nucleotide Nos. 1393–1395 in FIG. 3(b)) at its 3'-terminus. It is likely that the amino acid sequence I - G (or I'- G) in FIG. 3(a) is a transit peptide to chloroplasts by comparison with the squash ATase.

PREPARATION OF TRIAZINYL-BIS-ANTHRAQUINONE DYES BY REACTING ARYLDIHALOTRIAZINE WITH AMINO ANTHRAQUINONE

The present invention relates to an improved process for preparing anthraquinone dyes of the general formula I

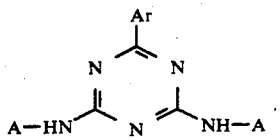

where Ar is aryl and the A radicals are each anthraquinonyl radicals, by reacting an aryldihalotriazine of the general formula II

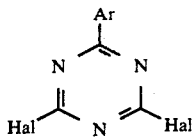

where Hal is chlorine or bromine, with an aminoanthraquinone III

A—NH$_2$  III in an organic solvent.

Anthraquinone dyes of the formula I belong to the important group of the vat dyes.

As is already known from DE patents 551,884, 637,937 and 1,026,456, the dyes I are obtainable by reacting the aryldichlorotriazines II with the aminoanthraquinones III in a high-boiling aromatic solvent such as nitrobenzene or di- or trichlorobenzene. However, the yields of from 85 to 90% obtainable with this process are unsatisfactory.

Attempts to improve the process by including bases and a copper(I)amine catalyst (DE patent 1,795,102) had only limited success and in the case of the particularly important dye Vat Blue 66 (Ar = phenyl, A = 1-amino-2-acetylanthraquinon-4-yl) led even to a yield of only 53%.

It is an object of the present invention to make available the dyes I in better yields and in a more economical manner.

We have found that this object is achieved by a process for preparing an anthraquinone dye of the general formula I

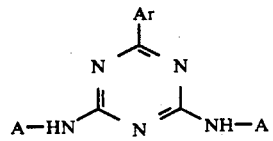

where Ar is aryl and the A radicals are each anthraquinonyl, by reacting an aryldihalotriazine of the general formula II

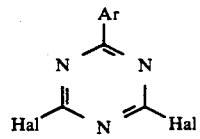

where Hal is chlorine or bromine, with an aminoanthraquinone III

A—NH$_2$  III in an organic solvent, which comprises using as solvent for this purpose an N—C$_1$-C$_4$-alkylpyrrolid-2-one, N—C$_1$-C$_4$-alkylpiperid-2-one, N-di-C -C -alkylacetamide or N-di-C$_1$-C$_4$-alkylpropionamide or a urea derivative of the formula IV

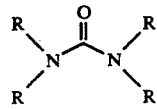

where the radicals R are identical or different alkyl groups of from 1 to 4 carbon atoms which can also be linked to one another to form a 5- or 6-membered ring containing the urea group.

Suitable solvents for the purposes of the present invention are

N-C$_1$-C$_4$-alkylpyrrolid-2-ones such as N-ethyl-, N-n-propyl-, N-isopropyl- or N-n-butyl-pyrrolidone, preferably N-methylpyrrolidone, N-C$_1$C$_4$-alkylpiperid-2-ones, such as N-ethyl-, N-n-propyl-, N-isopropyl- or N-n-butylpiperidone, preferably N-methylpiperidone, urea derivatives of the formula IV with 4 identical or different C$_1$-C$_4$-alkyl groups as radicals R such as tetra-n-propyl-, tetra-n-butyl- or dimethyldiethylurea, preferably tetramethyl- or tetraethyl-urea, or with radicals R which link together as ethyleneor propylene-ureas to form a 5- or 6-membered ring containing the urea group, such as 1,3-diethyl- or 1,3-dipropyl-imidazolidin-2-one or 1,3-diethyl- or 1,3-dipropyl-tetrahydro-2(1H)-pyrimidinone, preferably 1,3-dimethylimidazolidin-2-one or 1,3-dimethyl-tetrahydro-2(1H)-pyrimidinone, and N-di-C$_1$-C$_4$-alkyl-acetamides or -propionamides such as diethyl-, di-n-propyl- or di-n-butyl-acetamide or dimethyl-, diethyl-, di-n-propyl- or di-n-butylpropionamide, preferably dimethylacetamide.

These solvents are very potent solvents for the starting materials of the process. Thus, the amount of solvent is in general only 2–6, preferably 2.5–4 kg per kg of III.

The reaction can also be carried out in the presence of acid-binding agents such as the alkali metal salts of weak acids, for example sodium acetate, sodium carbonate or potassium carbonate.

Furthermore, it is also possible to use a catalyst in the form of an addition compound of copper(I) iodide or bromide with a tertiary base such as triethylamine, pyridine or related compounds.

The starting compounds II an III are known or obtainable by known methods. The molar ratio of II to III is advantageously from 0.5:1 to 1:1, in particular from 0.6:1 to 0.8:1.

In general, the reaction is carried out at from 80 to 200° C., preferably at from 100 to 160° C. The reactants can be added alternatively before or after the reaction temperature has been reached. It is also possible to increase the temperature during the reaction in order to achieve complete conversion.

The reaction is in general carried out under atmospheric pressure but can also be carried out under reduced pressure.

The reaction times including the after-stirring times are in general from 5 to 12, preferably from 6 to 8, hours.

A solution of a mol of an aminoanthraquinone III and b g of a solvent S was admixed at $T_1°$ C. with 0.18 mol of 2-phenyl-4,6-dichloro-1,3,5-triazine (II) in the course of 45 min, maintained at $T_1°$ C. for $t_1$ hours and, following a heating-up time of 2 h, subsequently stirred at $T_2°$ C. for $t_2$ hours.

Then the solution was cooled down to 60–70° C., the dye I forming a precipitate. The precipitate was separated off, washed initially with solvent S and then with water and thereafter dried.

The details of these experiments and the results thereof are summarized in the following table:

TABLE

| Example | Anthraquinone III | a mol | Solvent S | b g | $T_1$ °C. | $t_1$ h | $T_2$ °C. | $t_2$ h | Yield of I |
|---|---|---|---|---|---|---|---|---|---|
| 1 | 1,4-diamino-2-acetyl | 0.27 | N-methylpyrrolid-2-one | 250 | 120 | 2.5 | 150 | 2 | 98% |
| 2 | 1,4-diamino-2-acetyl | 0.27 | N-methylpyrrolid-2-one | 190 | 120 | 2.5 | 150 | 2 | 98% |
| 3 | 1,4-diamino-2-acetyl | 0.27 | N-methylpyrrolid-2-one | 375 | 120 | 2.5 | 150 | 2 | 98% |
| 4 | 1,4-diamino-2-acetyl | 0.27 | N-methylpyrrolid-2-one | 250 | 100 | 3 | 150 | 2 | 98% |
| 5 | 1,4-diamino-2-acetyl | 0.27 | N-methylpyrrolid-2-one | 250 | 130 | — | 130 | 4–5 | 98% |
| 6 | 1,4-diamino-2-acetyl | 0.27 | N-methylpyrrolid-2-one | 250 | 160 | — | 160 | 4–5 | 98% |
| 7 | 1,4-diamino-2-acetyl | 0.27 | 1,3-dimethyl-imidazolid-2-one | 250 | 120 | 2.5 | 150 | 2 | 94% |
| 8 | 1,4-diamino-2-acetyl | 0.27 | 1,3-dimethyltetrahydro-2(1H)-pyrimidin-2-one | 250 | 120 | 2.5 | 150 | 2 | 92% |
| 9 | 1,4-diamino-2-acetyl | 0.27 | tetramethylurea | 250 | 120 | 2.5 | 150 | 2 | 92% |
| 10 | 1-amino | 0.24 | N-methylpyrrolid-2-one | 250 | 120 | 2.5 | 150 | 2 | 72% |
| 11 | 2-amino | 0.24 | N-methylpyrrolid-2-one | 250 | 120 | 2.5 | 150 | 2 | 92% |

The reaction mixture is worked up for the products in a conventional manner, preferably by cooling the solution and separating off the precipitating dyes I and washing them or by distilling the solvent out of the reaction mixture.

The dyes I are obtained in very high purity and distinctly better yield than heretofore.

Since the solvent, after separation from the dyes I, is obtained in a water-free or at least low-water form and thus is readily regenerable, moreover, water pollution is kept to a minimum.

The process of the present invention is of particular importance for those dyes I where Ar is for example chlorophenyl, dichlorophenyl, bromophenyl, tolyl, methoxyphenyl, ethoxyphenyl or dimethylaminophenyl, preferably phenyl, and which are derived from the following aminoanthraquinones III:

1,4-, 1,5-, 1,8- or 2,6-diaminoanthraquinones, 1-amino-4-alkoxyanthraquinones, preferably 1-amino-4-methoxyanthraquinone, 1-amino-4-(or 5)-aroylaminoanthraquinones or chlorine, bromine or methoxy derivatives thereof, preferably 1-amino-5-benzoylaminoanthraquinone, preferably from 1- or 2-aminoanthraquinones or chlorine or bromine derivatives thereof, particularly preferably from 1,4-diamino-2-acetylanthraquinone.

A particularly preferred application of this process is the preparation of the abovementioned Vat Blue 66 dye.

EXAMPLES

Preparation of dyes of the formula

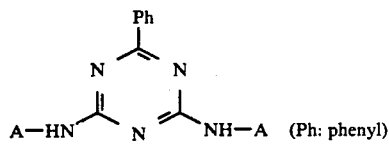 (Ph: phenyl)

We claim:

1. A process for preparing an anthrquinone dye of the formula

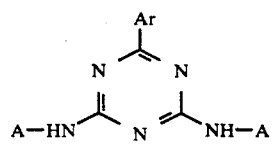

where Ar is aryl and the A radicals are each anthraquinonyl, by reacting an aryldihalotriazine of the formula

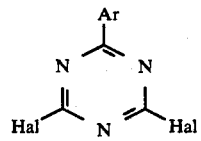

where Hal is chlorine or bromine, with an aminoanthraquinone of the formula

 [III]

in an organic solvent selected from the group consisting of N-$C_1$-$C_4$-alkylpyrrolid-2-one, N-$C_1$-$C_4$-alkylpiperid-2-one, N-di-$C_1$-$C_4$-alkylacetamide, N-di-$C_1$-$C_4$-alkylpropionamide, a urea derivative of the formula

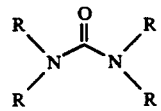

where the radicals R are identical or different alkyl groups of from 1 to 4 carbon atoms, 1,3-di-($C_1$-$C_4$-alkyl)-imidazolidin-2-one and 1,3-di-($C_1$-$C_4$-alkyl)-tetrahydro-2(1H)-pyrimidinone.